United States Patent [19]

Groshong et al.

[11] Patent Number: 4,529,399
[45] Date of Patent: Jul. 16, 1985

[54] METHOD AND APPARATUS FOR PLACING A CATHETER

[75] Inventors: LeRoy E. Groshong; Ronald J. Brawn, both of Portland, Oreg.

[73] Assignee: Catheter Technology Corporation, Salt Lake City, Utah

[21] Appl. No.: 491,257

[22] Filed: May 3, 1983

[51] Int. Cl.³ .................... A61M 5/00; A61M 25/00
[52] U.S. Cl. ................................ 604/53; 604/159; 604/170; 604/900
[58] Field of Search ................................ 604/51–53, 604/158–163, 170, 280, 900

[56] References Cited

U.S. PATENT DOCUMENTS

| | | | |
|---|---|---|---|
| 3,000,380 | 9/1961 | Doherty | 604/159 |
| 3,185,152 | 5/1965 | Ring | 604/159 |
| 3,685,513 | 8/1972 | Bellamy | 604/159 |
| 3,792,703 | 2/1974 | Moorehead | 604/158 |
| 4,147,165 | 4/1979 | Tauschinski | 640/161 |
| 4,327,722 | 5/1982 | Groshong et al. | 604/53 |
| 4,464,171 | 8/1984 | Garwin | 604/53 |

FOREIGN PATENT DOCUMENTS 1457344 11/1966 France ................ 604/159

Primary Examiner—Dalton L. Truluck
Attorney, Agent, or Firm—Klarquist, Sparkman, Campbell, Leigh & Whinston

[57] ABSTRACT

The skin and a subjacent body vessel is pierced with a needle mounted on a fluid-fillable chamber at the opposite end of which is a plunger movable into the chamber. In one embodiment, disposed within the needle and chamber is a closed-ended flexible catheter. A flexible stylet is disposed in the catheter. The catheter is drawn through the needle and into the body vessel by pushing into the chamber the plunger which engages the distal portion of the stylet. The closed-ended pliable catheter is drawn into place in the body vessel by the pushing stylet while fluid is simultaneously infused into the body vessel to dilate it and thereby ease the advancement of the catheter with minimal damage to the vessel wall.

The chamber and needle are removable from the catheter, leaving it in place in the body for the infusion of fluid.

In another embodiment a stiffer, open-ended catheter is used and plunger pushes directly against the catheter to push it into the body vessel.

10 Claims, 5 Drawing Figures

U.S. Patent  Jul. 16, 1985  4,529,399
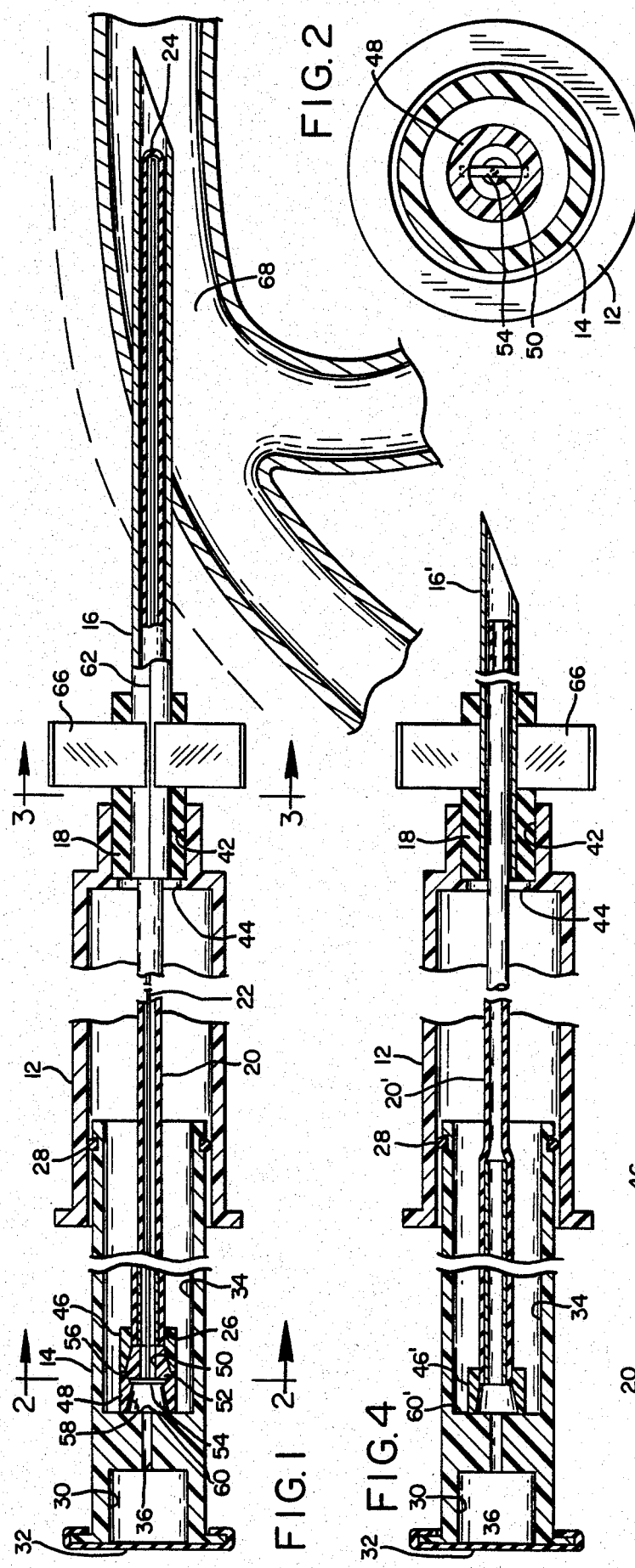
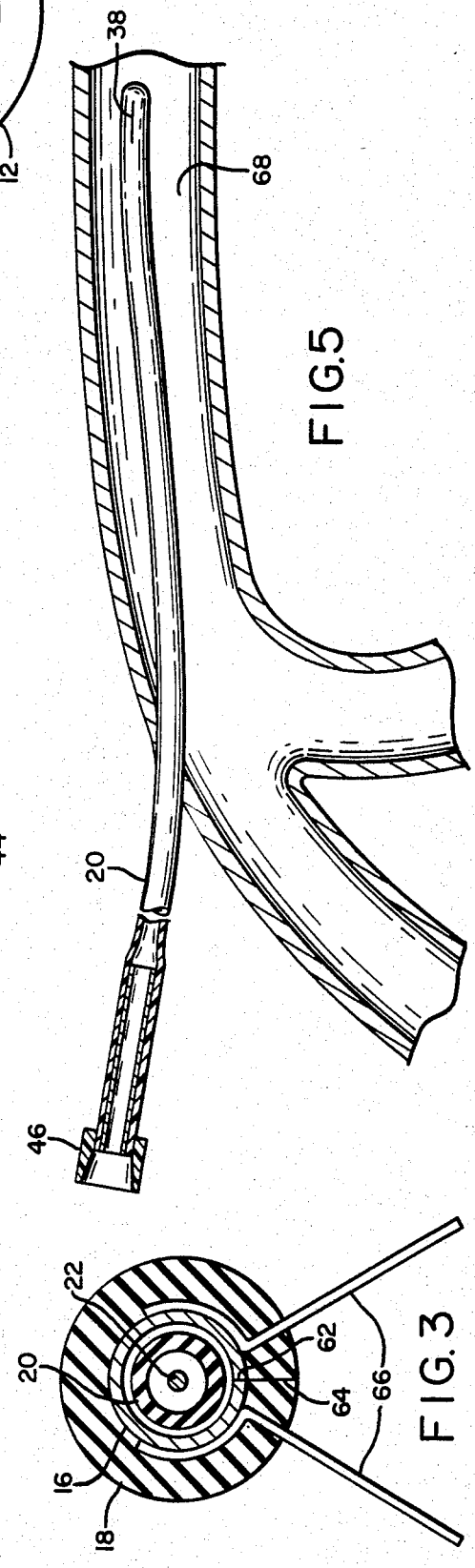

METHOD AND APPARATUS FOR PLACING A CATHETER

BACKGROUND OF THE INVENTION

This invention relates generally to the percutaneous placement of catheters into body vessels and more particularly to a method and apparatus for simple aseptic percutaneous placement of extremely flexible, thin-walled, closed-ended catheters.

Flexible and resilient intravascular catheters have in the past been inserted and used for a wide variety of medical purposes. For example, catheters have been used for intravenous volume support, for intravenous nutrition including hyperalimentation, for administration of therapeutic fluids and drugs, and for repeated withdrawal of body fluids for laboratory analysis.

Various methods have been utilized to insert such catheters into body vessels. With respect to such insertion methods the term "distal end" refers to the rearward end of the catheter, needle, or other member which is normally situated externally of the patient's body. The term "proximal end" refers to the forward end of the catheter, needle, or other member which is inserted into the patient's body or which is disposed closer to the body than the distal end.

Flexible and resilient catheters may be surgically placed in an appropriate body vessel by exposing the vessel, incising the vessel wall, and inserting the catheter through the surgical incision. This method is less desirable than other alternatives because of the time and expertise required, the patient discomfort, and the risk of infection.

A more common technique of inserting catheters into body vessels utilizes a stiff but thin walled catheter which fits snugly over a hollow beveled needle such that the needle acts both to penetrate the epidermis and subjacent body vessel and as a guide and stiffener over which the catheter is advanced into the vessel. This method of catheter placement, although widely utilized, has several disadvantages. For one, the catheter material must have a significant degree of stiffness so that it can be advanced easily past the proximal end of the internal needle and into the vessel without bending or intussuscepting. This degree of stiffness does not allow the catheter to conform easily to curves and bends of the vessel thus causing possible damage to the vessel wall, and even vessel perforation, during catheter advancement. After insertion irritation of the vessel lining by the stiff catheter may result in inflammation and blood clot formation.

Such stiff catheter material has decreased elastic memory and thus tends irreversibly to kink upon sharp or repeated bending, resulting in catheter obstruction and failure. The tendency to kink prevents the use of this catheter type across joint spaces and other anatomic locations in which repeated flexion and extension motions are expected unless additional precautions are taken such as joint splinting or immobilization of the anatomic area of catheter insertion.

Another disadvantage of this "over-the-needle" method of catheter insertion is that the external surface of the catheter is in direct contact with the surrounding epidermis throughout the insertion procedure and thus as the catheter is advanced into the vessel it may carry epidermal bacteria into the subcutaneous tissue and possibly the vessel which may then cause tissue and vessel infection. After insertion the stiff catheter has a tendency to slide in and out of the epidermal insertion site during voluntary or involuntary motion of the tissue through which the catheter is inserted, thus leading to the likely continued intermittent introduction of epidermal bacteria into the subcutaneous tissue space.

Yet a further disadvantage of the "over-the-needle" approach is that the catheter must of necessity be open ended. This allows retrograde blood flow into the open proximal end of the catheter which may result in clot formation within the catheter lumen with subsequent catheter failure, requires continuous flow of fluid through the catheter or repeated catheter flushing to prevent such clot formation, and also allows the possibility of hermorrhage through the open ended catheter should the distal end become loosened or disconnected.

Another method of catheter insertion uses a hollow metal needle to penetrate the epidermis and subjacent body vessel; through the lumen of such introducing needle the catheter is inserted and advanced. Such catheters must be relatively stiff to allow facile advancement of the catheter through the introducing needle and into the vessel. As such they suffer the disadvantages previously described for relatively stiff intravascular catheters. Said catheters are not, however, required to be open-ended. Because the catheter is generally advanced manually through the introducing metal needle, it is free to move both forward and backward within said needle thus allowing, either inadvertently or purposefully, retrograde catheter motion across the sharp introducing needle bevel causing possible catheter nicking or shearing. The result may be damage to the catheter wall or complete shearing off of the catheter end with such piece passing centrally in the vascular system and causing serious medical consequences.

Because an appropriate female fluid flow adaptor to allow connection to a fluid source is conventionally positioned on the distal end of the catheter, the introducing needle must frequently remain proximal to the adaptor, around the catheter, and remain on the patient with a protective device such that the sharp needle is prevented from cutting or shearing the catheter with adverse results. Alternatively, the introducing needle may be of a type such as shown in U.S. Pat. No. 3,598,118 which can be split lengthwise and removed from around the catheter. A variation of this technique which does not require a splittable needle is described in U.S. Pat. No. 4,068,659 to Moorehead. In this method the fluid flow adaptor is applied to the catheter subsequent to catheter insertion and removal of the inserting needle.

Yet another method of catheter placement requires inserting a hollow metal needle into a body vessel, introducing a stiff guidewire through said needle into a body vessel, removing the needle, and threading the catheter over the guidewire percutaneously into the body vessel to a desired distance. After catheter placement the guidewire is removed. This method requires a catheter which is both open-ended and relatively rigid, thus having the associated potential problems and complications previously enumerated. In addition, the insertion technique is not completely sterile in that the external surface of the catheter is drawn through the epidermis thus causing epidermal bacteria and organisms to be drawn into the subcutaneous tissue and possibly into the body vessel by the outer wall of the catheter. In our U.S. Pat. No. 4,327,722, we describe a method of inserting a soft, flexible closed-ended catheter wherein a stiffener in the form of a stainless steel wire is inserted in the catheter and pushed to cause the catheter to be drawn into the vein.

It is thus an object of the present invention to provide an improved method and apparatus for percutaneous placement of a closed-ended catheter fabricated of extremely flexible, biocompatible material such as thin-walled silicon rubber or similar material.

It is yet another object of the present invention to provide a method of percutaneously inserting a catheter in a completely sterile fashion without the possibility of catheter contamination by operator handling or by the skin through which the catheter must pass.

Another object is to provide a placement procedure in which the operator can test the position of the inserting needle within the body vessel as the catheter is being advanced into said vessel. He can thus verify that the introducing needle and the catheter are continuously disposed in the body vessel and have not become dislodged.

It is also an object to provide a method and apparatus for placing an infusion catheter in which sterile injection fluid, i.e., liquid can be infused through the catheter and into the body vessel during catheter placement. Such fluid injection will tend to dilate and expand the vessel into which the catheter is being advanced and thus facilitate catheter placement. Such fluid injection should, of course, avoid the possibility of introducing air into the bloodstream which could result in air embolism with adverse medical consequences.

It is also desirable that the method and apparatus of placing the catheter be usable in both peripheral and central venous applications. Yet another object of the invention is to provide a method and apparatus for percutaneously placing an infusion catheter which permits rapid insertion of the catheter to facilitate emergency usage, yet which results in minimum catheter trauma to the wall of the body vessel into which the catheter is being advanced. Such method and apparatus desirably dilate the blood vessel to ease advancement of the catheter therethrough.

SUMMARY OF THE INVENTION

In accordance with the present invention, the skin and a subjacent body vessel is pierced with a needle mounted on a liquid-filled chamber at the opposite end of which is a plunger movable into the chamber. Disposed within the needle and chamber is the catheter, preferably of the closed end type described in our co-pending patent application entitled "Two-Way Valve Catheter". A stylet in the form of flexible stainless steel wire is disposed in the catheter. The catheter is drawn through the needle and into the body vessel by pushing into the chamber the plunger which engages the distal portion of the stylet, the pushing stylet having a proximal end extending against the inner proximal closed end of the catheter. Thus, the closed-ended pliable catheter is drawn into place in the body vessel by the pushing stylet while liquid in each is simultaneously infused into the body vessel to dilate it and thereby ease the advancement of the catheter with minimal damage to the vessel wall.

The chamber and needle are removable from the catheter leaving it in place in the body for the infusion of liquid in each.

BRIEF DESCRIPTION OF THE DRAWINGS

FIG. 1 is a longitudinal sectional view of the invention showing the same with the needle positioned in a body vessel in preparation for insertion of the catheter;

FIG. 2 is an enlarged sectional view taken along line 2—2 of FIG. 1;

FIG. 3 is an enlarged sectional view taken along line 3—3 of FIG. 1;

FIG. 4 is a longitudinal sectional view of a modified form of the invention; and FIG. 5 is a view of the catheter of the embodiment of FIGS. 1-3 when fully inserted into a body vessel and in condition for attachment to a fluid source.

DETAILED DESCRIPTION OF THE PREFERRED EMBODIMENTS

In accordance with the embodiment of the invention illustrated in FIGS. 1 and 2, the apparatus of the invention comprises a syringe-like barrel or body 12 having a plunger 14 slidably mounted to the distal end thereof. A hollow metal needle 16 is releasably affixed to the proximal end of the syringe body 12 by an appropriate bushing 18 on the distal end of the needle. In the initial condition of the apparatus, a closed-ended catheter 20 is disposed wholly within the needle 16, syringe barrel 12, and plunger 14, as shown in FIG. 1. Positioned within the catheter is an internal pushing stylet 22 in the form of a flexible stainless steel wire which extends the full length of the catheter from the closed proximal end 24 to the distal end 26 of the catheter.

An appropriate fluid seal such as an O-ring 28 is disposed between the plunger 14 and syringe body 12. The outer end of the plunger 14 is formed with a cavity 30 closed by a membrane 32. The opposite end of the plunger 14 is formed with a chamber 34 which is in communication with the cavity 30 through a passage 36. Fluid may be infused into the chamber 34 through an hypodermic needle or the like inserted through the membrane 32.

The catheter 20 may be of the type described in our U.S. Pat. No. 4,327,722, and preferably is of a two-way valve type, permitting flow in two directions as is described in detail in our co-pending patent application Ser. No. 491,258, filed May 3, 1983. The catheter 20 includes a slit 38 (see FIG. 5) adjacent the proximal end of the catheter to provide an opening through which liquid may pass out of the catheter. The catheter 20 is preferably fabricated of a soft, flexible, biocompatible material such as silastic rubber sold by Dow-Corning under the trademark SILASTIC. This material is extremely elastic and soft.

The needle 16 preferably is of a longitudinally splittable type with a resilient bushing 18 on its distal end which is compressively inserted in a cup 42 formed on the proximal end of the body 12, surrounding an opening 44 in the end wall of the body.

Means are provided for applying a force to the distal end of the stylet 22 to cause the catheter to be drawn by the stylet into a body vessel. The illustrated means includes a female adaptor coupler element 46 which is fixedly attached to the distal end of the catheter 20 and is slidably positioned within the plunger chamber 34. Fitting cooperatively within the coupler element 46 is a second coupler element 48. Both coupler elements are preferably of lesser diameter than opening 44. The distal end of the stylet 22 extends through a central opening 50 in the bottom 52 of coupler element 48 and is provided with a cross element 54 the opposite ends of which are engaged in a recess 56 provided in the side wall of the coupler 48. As illustrated, the coupler elements 46, 48 have substantial clearance between them and the inner wall of the plunger 14 so as not to impede liquid flow around the elements. Likewise, the cross element 54 allows for liquid flow through the opening 50. The top of the element 48 is formed with a frustoconical chamber 58 which communicates with the central opening 50.

As will be apparent when the plunger 14 is moved inwardly of the syringe body 12, the end wall 60 of the chamber 34 will engage the upper end of the coupler element 48 causing it to move relative to the body 12. Since the end 54 of the stylet 22 is engaged in the coupler element 48, the stylet will be forced out of the needle carrying with it the catheter 20.

As indicated above, the needle 16 preferably is of the splittable breakaway type and as such is formed with a longitudinal slit 62 along one side extending the full length of the needle. The bushing 18 is provided with a corresponding slit 64. Fixed to the needle 16 are a pair of wing-like arms 66, one on each side of the slit 62 and which protrude up through the bushing 64. By pushing the arms 66 apart the needle and bushing can be opened up along the slits 62, 64 to permit the needle 16 to be removed from the catheter by sliding it sidewise relative to the catheter. The needle is preferably coated with a thin polymeric film to prevent air or fluid leaks along the needle slit, but not so as to interfere with the needle splitting function.

OPERATION OF THE FIRST EMBODIMENT

To use the above-described apparatus the syringe chamber body 12, plunger 14, and needle 16 are preferably filled with sterile, biologically compatible liquid. This may be done by inserting the needle of a liquid filled syringe through the membrane 32 and forcing liquid from the syringe into the cavity 30 from whence it will flow to the syringe chamber 34 and into the syringe body 12. This also fills the catheter 20 with liquid. At this point the catheter 20 with internal pushing stylet 22 therein will be disposed within the liquid-filled syringe body 12, plunger 14, and attached needle 16, as shown in FIG. 1, the plunger 14 being positioned adjacent the wall 60.

The apparatus is now ready for placement of the catheter 20 in a body vessel 68 schematically shown in phantom in FIG. 1. To initiate placement the skin 70 and subjacent body vessel 68 of the patient are pierced by the needle 16. To confirm the position of the end of the needle 16 within the body vessel 68, the plunger 14 may be withdrawn slightly relative to syringe body 12 so that body fluid will reflux ("flash") through the needle 16 and the catheter 20 into the syringe body 12 and be seen by the operator, thus confirming that the end of the needle 16 is properly positioned. The plunger 14 is then advanced into the syringe body, impinging upon coupler element 48 and thus pushing upon the distal end of stylet 22. Since the proximal end of the stylet 22 engages the closed internal proximal end 24 of the catheter 20, the catheter will be drawn out of the needle 16 and into the body vessel 68. If, again, the operator wants to determine that the needle 16 and catheter 20 are still disposed within the blood vessel 68, the plunger 14 may be slightly withdrawn to cause reflux of body fluid into the syringe body chamber. Because the distal end of the catheter pushing stylet is not affixed to the proximal end of the plunger 14, withdrawal of the plunger to reflux fluid will not cause the pushing stylet 22 or the catheter 20 to be withdrawn from the body vessel 68 or move with respect to the needle 16. Thus, the catheter will not be cut or damaged by retrograde motion against the sharp proximal bevelled end of the needle. Once it is confirmed that the needle is properly positioned by noting reflux of body fluid into the syringe chamber, the operator may resume depression of the plunger 14 until it is fully depressed or the catheter 20 is sufficiently extended into the body vessel 68. The simultaneous injection of liquid from the syringe body while the catheter 20 is being advanced allows for dilatation of the body vessel 68 such that catheter insertion is accomplished with a minimum of trauma to the body vessel.

When the catheter 20 is in its desired position, the needle 16 and syringe body 12 and plunger 14 are backed off from the catheter a distance sufficient to withdraw the needle from the patient. Next, the syringe body 12 is detached from the needle bushing 18 and removed along with plunger 14 by slipping the body off the catheter and over the coupler elements 46, 48. Next, the needle 16 and bushing 18 are opened up by appropriate manipulation of the arms 66 and the catheter 20 slipped out of the opened slit. Finally, the coupler element 48 is detached from the coupler element 46 and the stylet 22 withdrawn from the catheter 20, leaving the catheter installed in the body vessel 68 as schematically shown in FIG. 5 and with the coupler 46 available for connection to the male coupler of a source of liquid to be fed into the vessel 68.

In FIG. 4 there is illustrated a further embodiment of the invention which may utilize numerous of the elements described above. In this embodiment the body 12, plunger 14, and needle 16 may be substantially identical to the elements of like number previously described. However, in this embodiment the catheter 20' is formed of a material of sufficient stiffness that it can be inserted into a body vessel without the use of a stylet. The catheter 20' is illustrated as having an open proximal end, although a closed ended catheter could also be used. The catheter 20' is attached at its distal end to a coupler element 46' which in the initial condition of the apparatus is disposed immediately adjacent the end wall 60 of the plunger chamber.

To install the catheter 20', the needle 16 is inserted in a vessel as before described. When the needle has been properly positioned, the plunger 14 is advanced into the syringe body 12. This action causes the catheter to be advanced out of the needle and into the body vessel. When it is inserted to the desired depth, the needle 16, body 12, and plunger 14 can be removed from the catheter as described above, whereupon a source of liquid may be connected to the coupler element 46'.

As will be apparent, if a non-breakaway needle is utilized, it may not be removed from the catheter and must be immobilized and affixed to the body of the patient after it has been withdrawn.

The invention thus provides an apparatus and method which allow the percutaneous placement of a soft, flexible, closed-ended catheter affording no opportunity for catheter contamination by operator handling or by the epidermis through which the catheter passes, which allows no possibility of catheter damage by retrograde motion against the sharp needle through which the catheter is advanced, and which in a preferred embodiment facilitates catheter placement by hydrostatically dilating the blood vessel into which the catheter is being advanced.

Of course, it should be understood that various changes and modifications of the preferred embodiments described herein will be apparent to those skilled in the art. Such changes and modifications can be made without departing from the spirit and scope of the present invention and without diminishing its attendant advantages. It is, therefore, intended that such changes and modifications be covered by the following claims.

We claim:

1. A method for inserting into a body vessel a flexible catheter having a closed proximal end, comprising:
   piercing the skin and body vessel with a hollow needle mounted to one end of a liquid-filled chamber which contains a plunger at its opposite end and partially disposed within said chamber, said catheter having its proximal end positioned within said needle and its distal end positioned adjacent said plunger, an internal pushing stylet having proximal and distal ends positioned within said catheter and having its proximal end abutting the proximal closed end of the catheter and the distal end abutting said plunger,
   and drawing the catheter through the needle and into the body vessel by advancing said plunger into the chamber, whereby said plunger pushes said stylet which in turn pushes said catheter out of said needle so that said catheter is drawn from its closed proximal end into the vessel.

2. The method of claim 1 in which the chamber, needle, and plunger are filled with infusion liquid such that while the catheter is being advanced by forward motion of the plunger, liquid is simultaneously infused from the chamber into the body vessel so as to hydrostatically dilate the vessel and facilitate catheter advancement.

3. The method of claim 2 further comprising intermittently pulling back on the plunger while the needle is being inserted and while the catheter is being advanced into the body vessel to draw liquid from the body vessel into the chamber, thereby testing and confirming the needle position within the body vessel.

4. The method of claim 3 further comprising intermittently pulling back on the plunger while the catheter is being inserted, thereby testing and confirming the needle position within the body vessel.

5. An apparatus for inserting into a body vessel a catheter having a closed proximal end and an open distal end comprising,
   syringe means including a body defining a chamber, a hollow needle mounted to one end of said body in communication with said chamber, and a plunger slidably disposed in said chamber for movement between a first position adjacent the opposite end of said chamber and a second position adjacent said one chamber end,
   a closed-ended catheter having a proximal end and a distal end disposed within said chamber and needle, said catheter in the first position of said plunger having its proximal end positioned within said needle and its distal end positioned adjacent said plunger,
   a pushing stylet having proximal and distal ends positioned within said catheter with the proximal end of said stylet engaging the proximal end of said catheter and the distal end of said stylet abutting said plunger,
   whereby movement of said plunger from said first position to said second position causes said stylet to be pushed out of said needle and said stylet causes said catheter to be drawn out of said needle and into a body vessel into which said needle has been inserted.

6. The apparatus of claim 5 in which the chamber, needle and plunger are filled with sterile infusion liquid prior to catheter insertion whereby movement of said plunger to insert said catheter into a body vessel simultaneously causes said fluid to be injected into said vessel and around and through said catheter.

7. The apparatus of claim 5 wherein said pushing stylet distal end is freely movable away from said plunger whereby movement of said plunger toward said first position does not cause said catheter to be drawn retrograde through the inserting needle.

8. The device of claim 5 wherein the plunger has an axial channel through which infusion liquid may be directed into said chamber and needle.

9. The device of claim 5 wherein the needle is releasably mounted to said body.

10. The device of claim 5 wherein the needle is of a breakaway type which may be removed from around the catheter after catheter insertion has been completed.

* * * * *